United States Patent [19]
Gordon

[11] Patent Number: 5,833,701
[45] Date of Patent: *Nov. 10, 1998

[54] PROCEDURE AND DEVICE FOR CORRECTIVE AND THERAPEUTIC EYE TREATMENT

[75] Inventor: Eugene Irving Gordon, Mountainside, N.J.

[73] Assignee: Medjet, Inc., Edison, N.J.

[*] Notice: The term of this patent shall not extend beyond the expiration date of Pat. No. 5,556,406.

[21] Appl. No.: 712,582

[22] Filed: Sep. 13, 1996

Related U.S. Application Data

[63] Continuation of Ser. No. 304,245, Sep. 12, 1994, Pat. No. 5,556,406.
[51] Int. Cl.⁶ .................................................... A61F 2/14
[52] U.S. Cl. ........................ 606/166; 606/167; 604/20; 604/22
[58] Field of Search ................... 606/1, 2, 3–12, 606/166, 167; 604/22, 20

[56] References Cited

U.S. PATENT DOCUMENTS

| | | | |
|---|---|---|---|
| 4,856,513 | 8/1989 | Muller | 606/5 |
| 5,215,104 | 6/1993 | Steinert | 606/5 |
| 5,556,406 | 9/1996 | Gordon | 606/5 |
| 5,562,692 | 10/1996 | Bair | 606/1 |

FOREIGN PATENT DOCUMENTS

| | | | |
|---|---|---|---|
| 9322988 | 11/1993 | WIPO | 606/166 |

*Primary Examiner*—David M. Shay
*Attorney, Agent, or Firm*—Graham & James LLP

[57] ABSTRACT

A device and method for the selective removal of corneal tissue, and change of curvature thereof, for refractive vision correction, and for removal of corneal tissue for therapeutic treatment of the cornea; by means of a deforming template in conjunction with a water jet keratome. The template is adapted to deform the cornea to provide a regular surface which can be transversely cut by the water jet, while the cornea is supported against movement. The water jet can be adjusted to cleanly separate defective epithelium tissue from the Bowman's layer. Use of the water jet keratome provides a cut corneal tissue surface of smoothness and polish, substantially equivalent to that of the original surface, thereby enhancing healing and transplantation effectiveness.

11 Claims, 5 Drawing Sheets

PROCEDURE AND DEVICE FOR CORRECTIVE AND THERAPEUTIC EYE TREATMENT

This is a continuation in part of co-pending U.S. Ser. No. 304,245 filed Sep. 12, 1994.

FIELD OF THE INVENTION

This invention relates to methods and devices utilized in surgical procedures for therapeutic eye treatments and refractive vision correction and particularly to those procedures involving removal of corneal tissue to effect such treatments and corrections.

BACKGROUND OF THE INVENTION

Reshaping of the cornea, for refractive vision correction, has been the object of various procedures, some of which have only recently been developed to practical reality. In one well known procedure (radial keratotomy-RK), the cornea is incised with radial cuts outside the vision zone to flatten the anterior surface shape of the cornea in order to correct for myopia. This procedure, is however a surgical one, requiring a high degree of skill and judgment for effective and safe implementation. Additionally, the myopia-corrective flattening is usually not stable, even when properly done, with gradual progression to hyperopia over time.

In other, more recently developed procedures, a preselected portion of the anterior surface of the cornea (i.e. corneal tissue) is removed to change the effective curvature of the cornea with respect to image focusing. The change in cornea curvature is selected to provide the requisite refractive vision correction.

A relatively recently developed excimer laser-based system operates using a photochemical ablation, rather than by cutting. The sequence of incident laser pulses gradually removes the corneal tissue in successive steps. This method known as photorefractive keratectomy (PRK) is generally safe and effective and is approved by the FDA. However, there are several drawbacks, in addition to the high cost of the equipment, inherent with the PRK procedure. Foremost of the drawbacks is the error factor, or lack of achieved emmetropia, of sometimes more than ±1.0 diopter, as compared to the less than ±0.25 diopter error, typical with spectacles or contact lenses. In addition, use of the laser results in an imperfectly spherical corneal surface which sometimes reduces vision acuity. There are also long term effects relative to the physiology of the cornea and its interaction with the laser during ablation, which may result in the gradual reversal of the correction or which provide complications due to wound healing. There is also concern about possible long term mutagenic effects and retinal damage arising from acoustic shock waves generated during the ablative process.

To understand the effect of the various procedures used in treating the cornea, the physiology of the cornea must be taken into account. The cornea comprises a thin protective epithelium layer on top of the Bowman's membrane or layer, which in turn covers the major corneal stroma. Although the epithelium has no blood cells it does have nerve cell endings. When the corneal epithelium is eroded, cut, damaged, dystrophied or diseased, it can be removed and it will regenerate. The epithelium is also removed as a precursor to refractive surgery using a laser.

The cornea is subject to becoming partially or completely opaque as a result of various diseases of the main body of the cornea, with the treatment being partial or complete removal of the cornea and replacement with a donor cornea from an eye bank. Full transplants are performed by means of a device known as a trephine which comprises a circular blade which cuts completely through the cornea and exposes the interior portion of the globe. For partial transplants, a keratome is used to remove a partial thickness button or disc in a procedure known as lamellar keratoplasty. Partial transplants preserve the patient's own endothelium, the posterior layer of the cornea, avoiding replacing a sound endothelium with a typically older one that may be rejected by the recipient's body.

While the epithelium is regenerative, the Bowman's membrane is not. With ablative corneal tissue removal procedures, such as PRK, the epithelium and Bowman's membrane are removed together with a portion of the stroma. Subsequently, the epithelium regenerates on the exposed outer surface of the cornea but directly on the stroma, since the Bowman's layer is not regenerated. Direct regrowth of the epithelium on the stroma can however cause an undesirable corneal haze which gradually dissipates over time.

Removal of the epithelium alone, if necessary, is generally accomplished by means of scraping with a surgical blade. However, this is a rough, imperfect, and inaccurate means for removal of the epithelium and its use tends to damage the underlying Bowman's layer.

The Automated Lamellar Keratoplasty (ALK) surgical procedure preserves the epithelium and Bowman membrane and has been used for corrections of up to −20 diopters of myopia. This is in contrast to both the RK and PRK procedures, which, because of inherent instabilities and error factors, are usually not approved for correction of myopia of more than −6 diopters. In addition, PRK is not currently suitable for corrections other than myopia. In the ALK procedure there is an initial surgical removal, with a microkeratome, of a uniform thickness button or lenticule of corneal tissue of a thickness containing the epithelium layer, Bowman's membrane (intact) and a portion of the stroma. The button or lenticule preferably remains hingedly attached at one point to the cornea. The lenticule is moved out of the way, the stroma bed is then surgically reshaped, as required, and the lenticule is replaced, with good adherence and healing of the stroma-stroma surfaces and with the Bowman membrane being preserved, leaving the cornea clear. It appears that the stroma-stroma healing of the ALK procedure reduces, if not eliminates, wound healing instabilities, making this procedure the most suitable for large refractive corrections.

The use of a scalpel in the keratome requires that the intraocular pressure be elevated to an undesirably high level with attendant risk. Moreover, despite the advantage of retention of vision clarity and healing stability, the procedure is not very favored since it is complex, and potentially dangerous, requiring high surgical skill, is expensive, is usually inaccurate, with dependency on the surgeon's skill, and it can cause irregular astigmatism. These factors can be attributed to the structure, viscous nature and relatively generally unsupported character of a cornea, which makes use of a scalpel, or even a micro-keratome, difficult and highly subject to inaccuracies.

SUMMARY OF THE INVENTION

It is an object of the present invention to provide a method and device for the highly controlled cutting removal of corneal tissue for refractive correction, therapeutic keratoplasty, and selective removal of the epithelium for therapeutic eye treatment.

It is a further object of the present invention to provide a method and device for the vision correction and eye treatment, which embodies the advantages of the ALK procedures but with enhanced accuracy and reduced complexity.

It is another object of the present invention to provide such method and device with an accuracy at least comparable to that of spectacles or lenses and wherein the clarity and stability of the original corneal tissue is substantially retained.

It is a still further object of the present invention to provide a method and device for the accurate, selective removal of the corneal epithelium, without disturbing the Bowman's layer.

These and other objects, features and advantages will become more evident from the following discussion and the drawings in which:

SHORT DESCRIPTION OF THE DRAWINGS

DETAILED DESCRIPTION OF THE INVENTION

Figure 1:
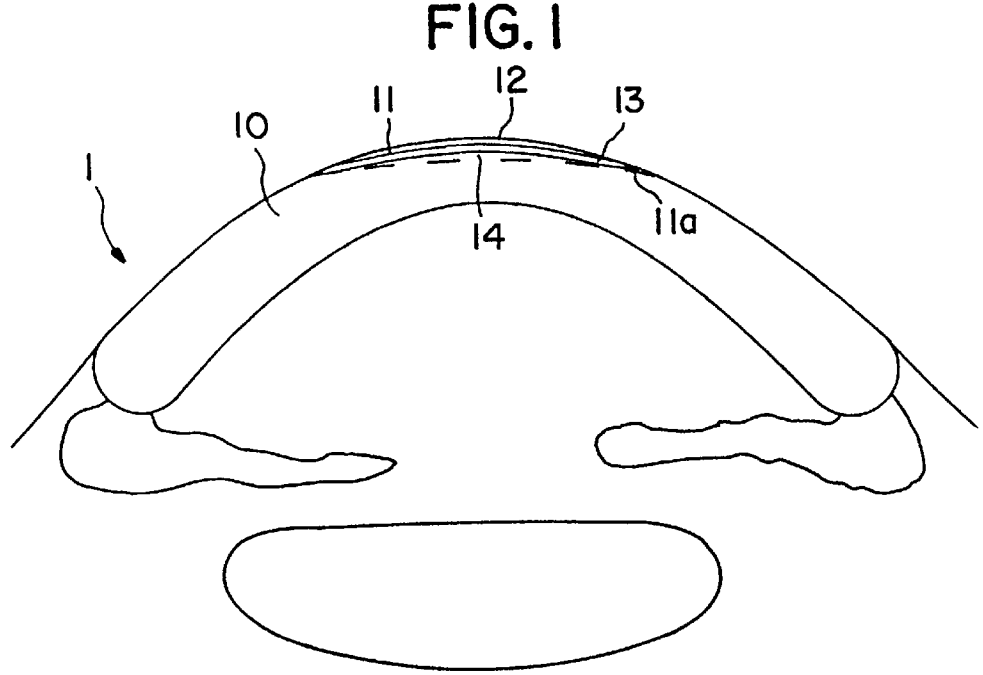
FIG. 1 is a representation of a side cross section view of an eye with the portion of the cornea to be removed, marked off.

Generally the present invention comprises a method and device for the selective, accurate removal of layers of corneal tissue, such as for keratoplasty, change of curvature thereof, for refractive vision correction of an eye and for selective removal of damaged, diseased or dystrophied portions of the cornea and, in particular, removal of epithelium without disturbing the Bowman's layer.

In accordance with the method of the present invention, for vision correction, the removal is effected by the steps of:
  a) determining the dimensions, shape and position of an anterior portion of the corneal tissue which is to be removed to provide the appropriate refractive vision correction or therapeutic removal or hinged flap;
  b) defining a surface, usually irregularly curved, along which the corneal tissue is to be cut for removal of the anterior portion of the corneal tissue, to provide the appropriate refractive correction or flap;
  c) deforming the anterior portion of the corneal tissue with deformation means whereby the surface to be cut assumes a planar or otherwise regular configuration; and
  d) cutting along the planar or regularly configured surface, with water jet cutting means.

With respect to treatment of the cornea by removal of defective tissue, it is the dimension, shape and position of the damaged, diseased, or dystrophied part of the cornea to be removed, which is determined, with a cutting surface being thereby defined for removal of such defective part of the cornea.

It is a phenomenon discovered herein that the epithelium and Bowman's layer have differing sectile characteristics, i.e., the Bowman's layer is harder and is thus more difficult to cut with a water jet. Accordingly, it is possible to appropriately adjust a water jet, in accordance with the present invention, to a pressure level sufficient to cut or erode epithelium tissue but not tissue of the Bowman's layer. This is an adjustment, with useful characteristics, not possible with use of a mechanical microkeratome, as currently utilized.

In order to effect selective removal of just the epithelium from the Bowman's layer, and in order to avoid disturbing the Bowman's layer, the water jet pressure is first adjusted to be sufficient to cut the epithelium but not the less sectile Bowman's layer, the cornea is then appropriately applanated, and the waterjet is positioned to cut at just above 40 microns (the nominal thickness of the epithelium). The waterjet will then cut at the interface between the epithelium and the Bowman's layer and erode away much of the remaining epithelial tissue. Some shaping of the applanator optimizes the shape of the removed epithelial region. Curving the template down at the output end increases the length of the region in the direction of the jet. This provides a clean separation between the layers, as may be needed for refraction correction or for therapeutic tissue removal from the cornea.

The anterior portion, as described above, for removal, also may include corneal stroma tissue which is removed beneath a lenticule or button, as in ALK procedures.

A device for use in effecting the method of the present invention comprises:
  a) means for providing a small diameter water jet of sufficient velocity and associated pressure whereby it is capable of laterally or transversely cutting corneal tissue;
  b) means for deforming the cornea to provide a regular interior surface, defining a plane or an arced surface, suitable for the controlled lateral movement cutting thereof by the waterjet, for cutting into or removal of a desired portion of corneal tissue; and
  c) means for stabilizing the corneal tissue against movement during said lateral cutting.

An applanation device such as a template member is preferably used as the deformation means. The template is adapted specifically to be placed and centered on the anterior portion of the corneal tissue to be removed, whereby it comprises a surface therein to which the anterior portion, to be removed, is adapted to be fitted or abutted and deformed by such fitting or abutment. Where suitable, such as for producing a parallel flap, the template may comprise a flat member.

The deformation is predeterminately controlled, such that the surface to be cut, at the base of this anterior portion assumes a planar or otherwise regular configuration (e.g., an arc segment of a circle), which is accessible for the cutting thereof. The fitted surface of the template has a height relative to a plane at the base of the template equal to the computed difference, point by point, of the difference in height between the anterior and posterior surfaces of the portion of the corneal tissue which is to be removed. The computed difference also should take into account geometrical distortion and tissue compression or extension. As a result, the posterior surface (i.e. the surface to be cut)

assumes a planar (or otherwise regular) configuration and the cut is effected by the lateral movement of a waterjet along a controlled path corresponding to the planar or regular surface.

For simpler cutting requirements (or wherein there is enhanced computer controlled cutting), the deformation means may even comprises a non-fitted flat plate with controlled compression of the cornea for predictable deformation.

In the initial determination of the dimensions, shape and position of the anterior portion of the corneal tissue (which is to be removed, to provide the appropriate refractive vision correction), the predictable effects of epithelium regrowth and wound healing, on the altered shape, should be taken into account.

For ease in providing a predictable cutting site for eye treatment and/of for different refractive corrections, a series or set of templates of appropriately differing shape and dimensions is used, though specifically adapted templates may be readily constructed, if necessary. Templates, including custom-made templates may be made in various ways including porous metal, such as sintered stainless steel, which can be appropriately formed with high accuracy milling techniques, e.g., electrostatic discharge machines.

The porous nature of the material is advantageous since it is preferred that the area into which anterior portion of the cornea is fitted, also functions as a "vacuum chuck" for the portion of the cornea to be removed, in order to ensure complete fitting and positive holding during the cutting step. It is preferred that vacuum suction means of suitable minimal suction strength be provided, through porous walls of the template, e.g. with micron sized pores therein, as formed from materials such as sintered stainless steel, in order to more closely conform and hold the anterior portion therewithin against the surface thereof. It is readily possible to coat a shaped surface with submicron particles of diamond or other hard material. This provides a highly adherent surface.

The shape of the template for a given desired correction depends on the relative position of the cutting plane and it is necessary that these portions be well established. The templates may be sintered stainless steel frits with high porosity exceeding 24% so that they will exhibit suction. A narrow circular gap at the circumference of the template provides adequate suction. Small diameter, glass thin wall tubes in a circular array with ends positioned to establish the template shape are another alternative. Typical template dimensions are 6 mm in diameter, with deviations of the surface from planarity of 150 microns or less. Another alternative is a system of small depressions in the template, that are connected to a vacuum.

The cutting means, is most preferably formed, by a circular nozzle orifice producing a high speed rectilinear water (sterile saline or water solution) jet beam driven by a water pressure of between 3000 to about 25000 psi and typically between 15000 to 20000 psi for lamellar cuts. The higher the pressure, the greater the speed of the water emitted from the nozzle and the smaller the diameter that may be used. A small diameter water jet beam of this character has been shown to provide a very smooth transverse cut in corneal tissue, with a smoothness similar to that of the original tissue surface. There is virtually no damage to the lamellar structure. Only the connecting collagen fibrils between lamellae are cut, allowing adjacent lamellae to separate with no damage, as observed in high magnification (5000×–35000×) electron microscopy. A selective pressure sufficient to cut epithelium tissue but not tissue of the Bowman's layer is about 1500, to 4500 psi, with water jet diameters ranging from 60 to 100 μm.

Since the water jet used in the cutting is of minimal size and amount of water, with substantially little or no disturbance of the tissue adjacent the cut, the water jet is readily utilizable in providing a partial rather than a complete through cut, whereby a hinged flap is formed without distortion, in the initial steps of the ALK type procedure. With respect to corneal tissue which is to be removed, because of the tissue fixation afforded by the template, and the minimal disturbance effected by the water jet, the cut tissue simply remains in place where it is removed by a separate procedure, such as by mechanical means.

A suitable diameter dimension of a cutting water jet is about 30 to 100 μm. The water jet may be controllably positioned and used via a ring member (i.e., globe fixation device) having a partial circumferentially disposed dispensing orifice therein. The ring member is adapted to be seated around the template on the globe (cornea or sclera) and positioned such that the dispensing slit or aperture is laterally aligned with the planar (or otherwise regular) cutting surface. After the template is positioned, activation and scanned movement of the water jet effects a damage free transverse cut of the corneal tissue, held by the template, in a fraction of a second and no more than several seconds. The ring further comprises a secondary opening opposite the orifice, for reception and removal of the water of the water jet. Water amounts in the range of about 0.5 to 3 ml are utilized in effecting the cutting procedure, depending on the pressure, the orifice diameter and the scan time which is dictated by the type of treatment with desired results.

In the preferred embodiment of the present invention, the water jet keratome has two main parts, aside from the water jet itself, of a cutting ring and the water jet beam template and its holder. This keratome is used in the following manner. The vertical meridian and center of the vision axis are identified by means similar to those in use for RK, and marked using a standard tool as used in RK. The cornea is viewed through the operating microscope. The cutting ring is placed on the globe (cornea or sclera) and centered and positioned relative to the marks on the cornea. Light suction is then applied to the cutting ring, thereby positioning it firmly on-the globe without substantially increasing the intra-ocular pressure. Thereafter the template and its holder are placed into the center of the cutting ring and locked into place. The template and the plane of the cut are thereby juxtaposed in an unambiguous repeatable manner and the cut is made relative to the template.

Because of the damage free nature of the cuts when effected by the waterjet as a Hydroblade™ keratome it is ideally utilized in therapeutic procedures such as described above. The thickness and diameter of a disc to be removed from the cornea can be predetermined and a replacement disc, cut to the same dimensions, is sutured in place, and will heal quickly and uniformly.

Uniformity and smoothness of the disc and the quality of the cut stromal bed provides for maximum effectiveness of healing thereafter and freedom from haze and irregular astigmatism.

DETAILED DESCRIPTION OF THE DRAWINGS AND THE PREFERRED EMBODIMENT

With specific reference to the drawings, in FIG. 1, a human eye 1 is shown in schematic cross section. Portion 11 of the cornea 10, marked off with dashed lines, has been calculated and predetermined to be removed for appropriate refractive vision correction. However, the base 11a of the portion to be removed 11, has a non-planar shape, which makes the accurate removal thereof, difficult to control. Portion 11 includes a section of the epithelium 12 and the Bowman's layer 13, as well as a segment of corneal stroma 14.

Figure 2:
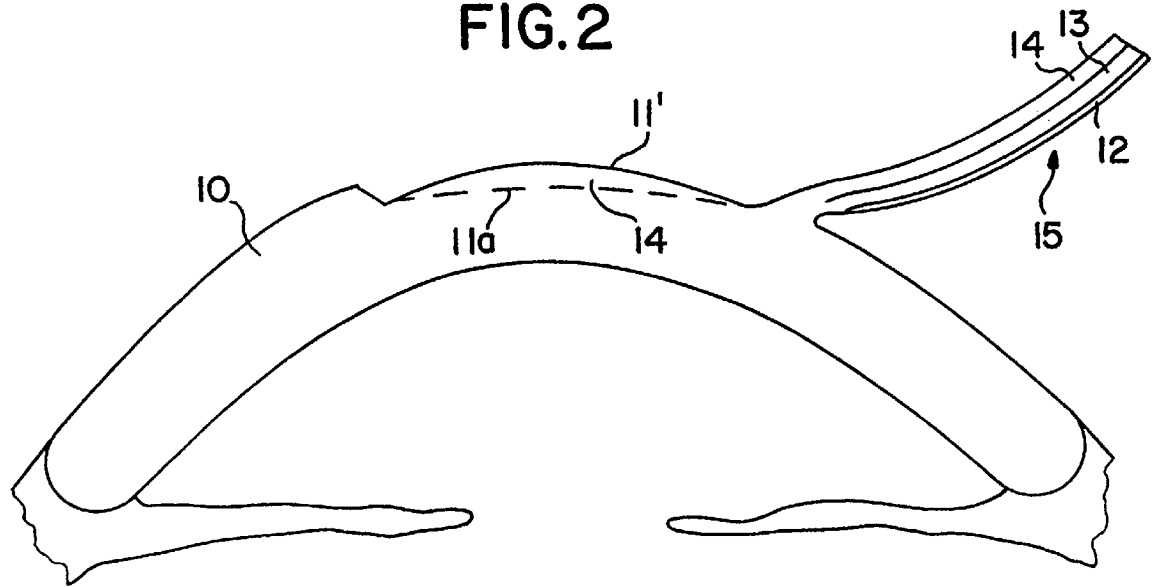
FIG. 2 shows a parallel lenticule of the outer corneal tissue being hingedly formed.

FIG. 2 illustrates the ALK type procedure wherein a lenticular flap 15, of epithelium 12, Bowman's layer 13 and corneal stroma 14 are hingedly moved out of position and cornea 10 is shown with portion to be removed 11', for the refractive vision correction. In this embodiment, portion 11' is comprised only of a segment of the corneal stroma 14, though the base 11a still embodies a curvature.

Figure 3:
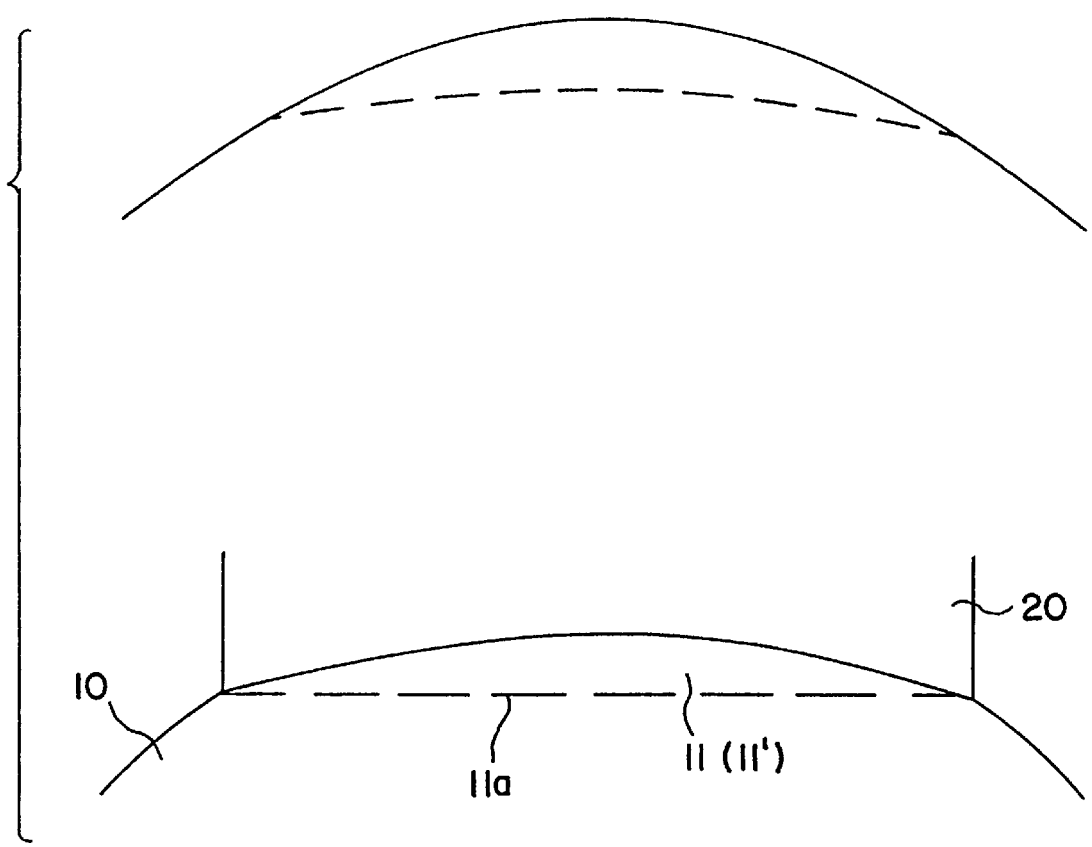
FIG. 3 depicts the placement of an applanating template on the portion of the cornea to be removed.
Figure 3A:
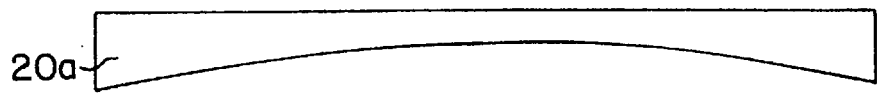
FIGS. 3a, 3b and 3c show, in cross-section, illustrative templates, as used for correction of myopia, hyperopia and astigmatism, respectively.
Figure 3B:
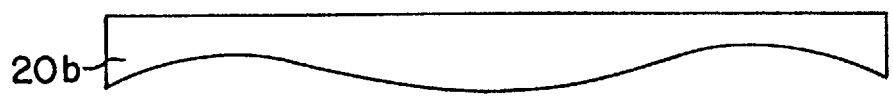
Figure 3C:
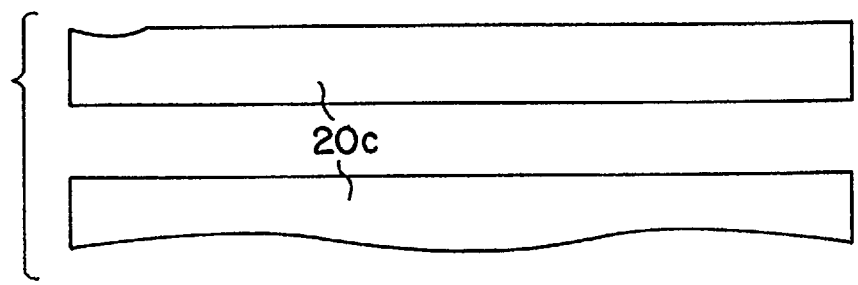
Figure 4:
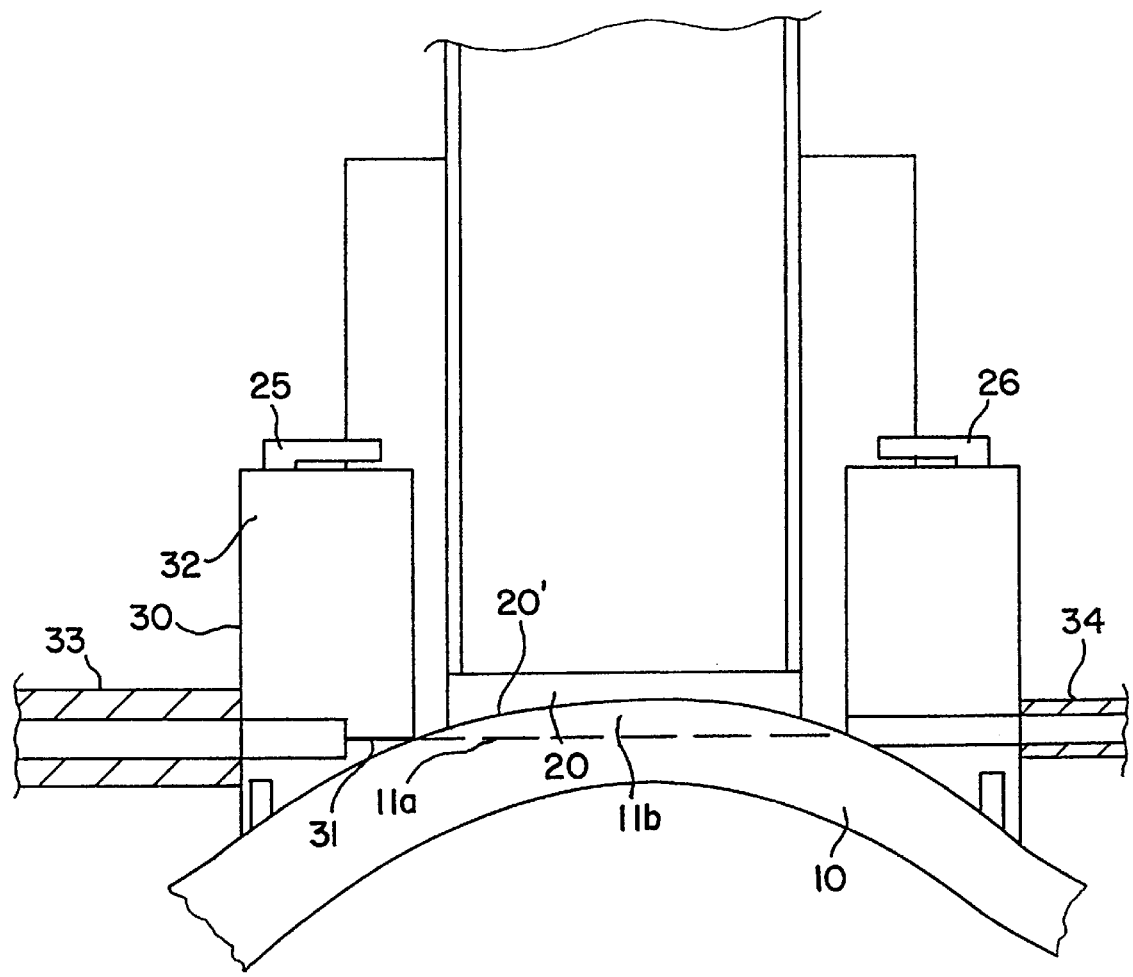
FIGS. 4 and 4a illustrate (side cross section and top view respectively) the use of a water jet and a cutting guide ring relative to the template and the corneal tissue to be removed.

In accordance with the present invention, in FIG. 3, template 20 is applied to either portion 11 or more preferably to portion 11', to deform the portion, on which it is seated, to provide base 11a with a planar surface conformation (as shown, or otherwise regular surface) suitable for cutting as shown in FIG. 4. As shown in cross section in FIGS. 3a–3c respectively, templates 20a–20c, illustrate templates used with: corrections for myopia, with decreased curvature (20a); correction for hyperopia, with increased curvature in the optical zone (20b); and with steepened curvature along the horizontal meridian (20c-shown with vertical and horizontal cross sections) for the correction of astigmatism. In each embodiment the respective template is adapted to the type of correction (myopia, hyperopia, and astigmatism) and to the degree of correction required. The respective templates 20a–c, when fitted, cause the portions, to be removed, to be deformed such that an externally exposed planar surface for cutting is formed, as shown in FIG. 3, at the base of the template.

Figure 4A:
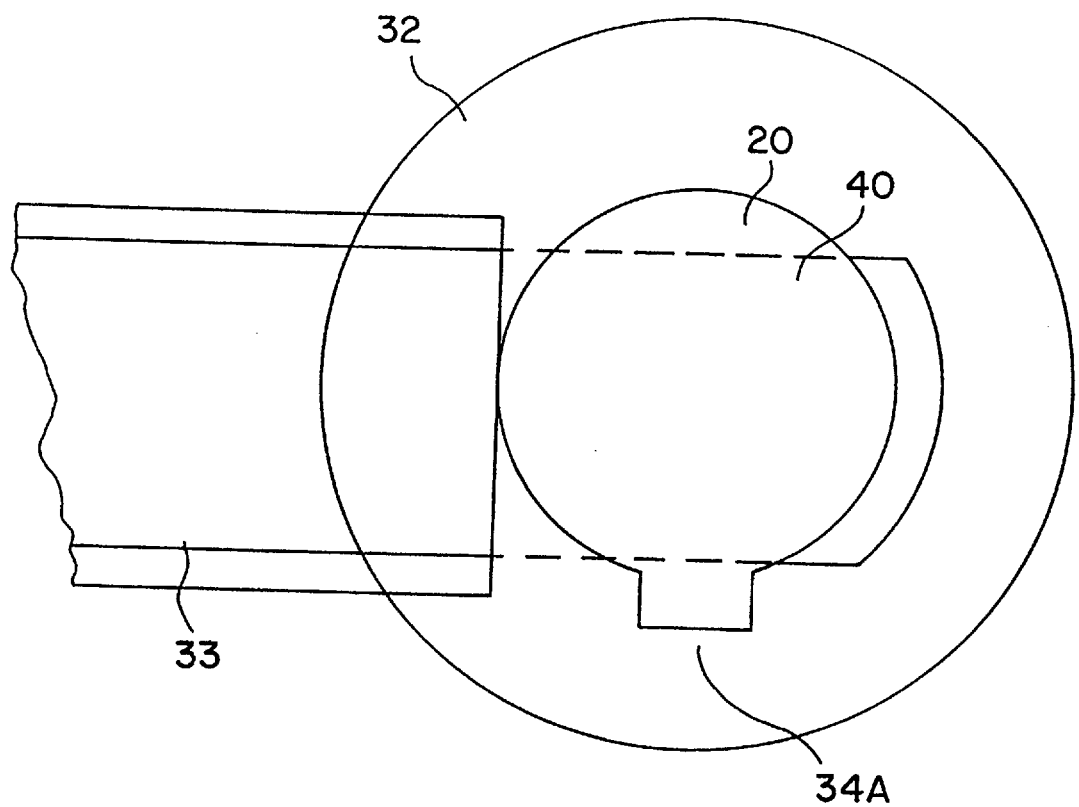

In FIGS. 4 and 4a, template 20, is shown as being positioned on cornea 10. Water jet cutting guide 30, is positioned relative thereto, such that planar surface 11a is exposed and aligned with water jet nozzle 31. The water jet cutting guide 30 is in the form of a ring 32, with water inlet 33, to nozzle 31, and water outlet 34. Template 20 is concentrically placed within the ring 32 and locked into position by locking tabs 25 and 26. To ensure that the deformation is effective in making the planar surface shown, a true surface for cutting (i.e., wherein, after the cutting, the cornea relaxes into the desired configuration), a suction vacuum is applied through the porous template or around the boundary of the template, to cause the cornea surface 11b to become closely conformed to template inner surface 20', with minimal compression of the cornea, preferably with tension. Minimal compression of the cornea is preferable in order to minimize erosion which occurs with cutting of a compressed cornea. The vacuum is maintained at least until the planar surface 11a has been cut. Since the cut is regular, e.g., planar in the embodiment shown, without erosion, and is effected by aligned controlled elements, and with the cornea being fully supported during the cutting, accuracy is very high. In addition, the water jet cut is without heat or abrasive elements. The cut planar surface retains the character of the original corneal tissue and preserves the integrity of all lamellae and the associated fibrils which are undamaged except as needed to change shape, in which case the lamellae and the associated fibrils are cut cleanly across.

After the cut is completed, the template and cutting ring are removed from the cornea. If the cut is effected without an ALK procedure, the corneal correction is complete. If an ALK procedure has been utilized (as shown in FIG. 4a, the ring 32 is provided with a keyway 34 to allow hinging of the lenticular flap 15 out of the way of the waterjet blade 40) the hinged lenticule is placed over the cut stroma tissue for healing in accordance with such known procedures.

Figure 5:
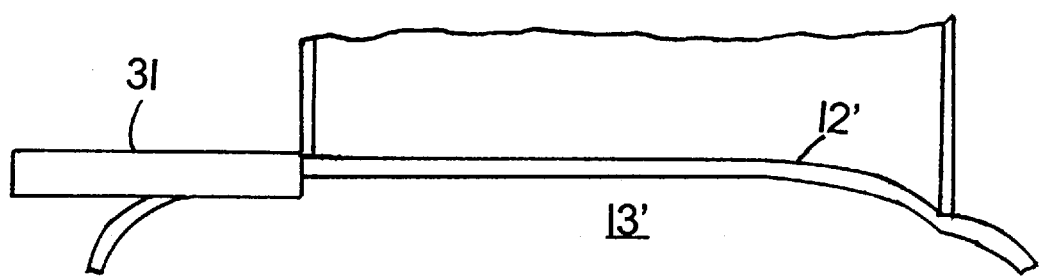
FIG. 5 depicts a selective removal of the epithelium from the Bowman's layer by means of the device of the present invention.

In therapeutic applications, and as shown in FIG. 5, a defective (eroded, cut, damaged, dystrophied or diseased) epithelium 12' or in preparation for various surgeries wherein a healthy epithelium must be removed, the epithelium is cleanly separated from Bowman's layer 13', by means of the water jet applied with a controlled speed and pressure, as defined above, whereby the water jet cuts the epithelium but not the Bowman's layer. As shown, the water jet is positioned at the approximate interface between the defective epithelium and the Bowman's layer and slightly towards the Bowman's layer. The water jet is self-guided to the interface between the Bowman's layer and the epithelium to effect a clean separation therebetween, whereby the defective epithelium can be cleanly removed. The epithelium regrows naturally in a few days.

It is understood that the details contained in the drawings and description are illustrative of the present invention and that changes may be made in procedure and with the devices utilized in effecting the procedure, without departing from the scope of the present invention as defined in the following claims.

I claim:

1. A device for the cutting of corneal tissue for any of therapeutic excision and refractive vision correction, said device comprising:

a) water jet means for providing a water jet of sufficient velocity and associated pressure to be capable of transversely cutting corneal tissue with an edge of the water jet, which edge is lateral to the direction of the water jet;

b) means for deforming the corneal tissue to provide a regular interior surface, defining a plane suitable for controlled lateral movement cutting thereof by the water jet, for cutting into or removal of a desired portion of corneal tissue; and c) means for stabilizing the corneal tissue against movement during said lateral cutting.

2. The device of claim 1, for use in the therapeutic removal of defective corneal tissue in an epithelium layer wherein the water jet means is capable of providing a water jet having a pressure and velocity sufficient to cut or erode tissue of the epithelium layer but not of a Bowman's layer adjacent thereto.

3. The device of claim 1, wherein the means for deforming the corneal tissue comprises a flat template.

4. The device of claim 1, wherein the means for deforming the corneal tissue comprises a template conformed to enclose an anterior section of the cornea.

5. The device of claim 3, wherein the template comprises means for minimizing compression of the corneal tissue.

6. The device of claim 3, wherein the template is adapted to remain on the cornea during the cutting of the corneal tissue and wherein the template comprises the means for stabilizing the corneal tissue against corneal movement during said lateral cutting.

7. A method for vision correction by removal of corneal tissue, comprising the steps of:

a) determining the dimensions, shape and position of an anterior portion of the corneal tissue which is to be removed to provide an appropriate refractive vision correction;

b) defining a surface, along which the corneal tissue is to be cut for removal of the anterior portion of the corneal tissue, to provide the appropriate refractive correction;

c) deforming the anterior portion of the corneal tissue with deformation means whereby the surface to be cut assumes a regular configuration; and d) transversely cutting along the regularly configured surface, with an edge of a water jet of said water jet cutting means which edge is lateral to the direction of the water jet.

8. The method according to claim 7, wherein the anterior portion of the corneal tissue is deformed with minimal compression.

9. A method of therapeutic corneal tissue removal wherein, the removal is effected by the steps of:

a) determining the dimensions, shape and position of an anterior portion of the defective corneal tissue which is to be removed;

b) defining a surface along which the corneal tissue is to be cut for removal of the defective corneal tissue;

c) deforming the anterior portion of the corneal tissue with deformation means whereby the surface to be cut assumes a planar or otherwise regular configuration; and d) transversely cutting along the planar or regularly configured surface, with an edge of a water jet of said water jet cutting means, which edge is lateral to the direction of the water jet, for removal of the defective corneal tissue.

10. The method of claim 9, wherein the defective corneal tissue comprises an epithelium layer of the cornea and wherein the epithelium layer is separated and removed from an adjacent Bowman's layer by using said water jet cutting means laterally directed at an approximate interface between the epithelium layer and the Bowman's layer and where pressure and speed of the water jet cutting means is adjusted to be sufficient to cut the epithelium layer tissue for removal thereof but insufficient to cut the Bowman's layer tissue.

11. The method of claim 10 wherein said pressure ranges between 1500 and 4500 psi, with water jet diameters ranging between 60 to 100$\mu$.

* * * * *